United States Patent [19]
Lee et al.

[11] Patent Number: 5,693,030
[45] Date of Patent: Dec. 2, 1997

[54] CATHETER AND METHOD OF INTRODUCTION

[75] Inventors: Jeffrey S. Lee, Dallas, Tex.; Miles D. Lee, Greeley, Colo.

[73] Assignee: Lee, Lee & Beal, Inc., Greeley, Colo.

[21] Appl. No.: 496,133

[22] Filed: Jun. 28, 1995

[51] Int. Cl.$^6$ ................................................. A61M 5/00
[52] U.S. Cl. ...................... 604/117; 604/161; 604/164; 606/1; 606/170
[58] Field of Search .................................. 606/194, 191, 606/192, 170, 1; 604/160, 93, 161, 167, 165, 175, 117, 96, 281; 128/772

[56] References Cited

U.S. PATENT DOCUMENTS

| | | | |
|---|---|---|---|
| Re. 31,855 | 3/1985 | Osborne | 604/161 |
| D. 247,975 | 5/1978 | Luther | D24/25 |
| 3,472,232 | 10/1969 | Earl | 604/160 |
| 3,550,591 | 12/1970 | MacGregor | 128/214.4 |
| 3,713,442 | 1/1973 | Walter | 128/214.4 |
| 4,147,165 | 4/1979 | Tauschinski | 128/214.4 |
| 4,412,832 | 11/1983 | Kling et al. | 604/164 |
| 4,576,589 | 3/1986 | Kraus et al. | 604/161 |
| 4,773,394 | 9/1988 | Reichstein et al. | 128/4 |
| 4,776,846 | 10/1988 | Wells | 604/161 |
| 4,883,468 | 11/1989 | Kousai et al. | 604/164 |
| 4,938,220 | 7/1990 | Mueller, Jr. | 128/658 |
| 4,983,168 | 1/1991 | Moorehead | 604/161 |
| 5,195,978 | 3/1993 | Schiffer | 604/161 |
| 5,250,059 | 10/1993 | Andreas et al. | 604/22 |
| 5,366,446 | 11/1994 | Tal et al. | 604/167 |
| 5,395,332 | 3/1995 | Ressemann et al. | 606/194 |
| 5,405,341 | 4/1995 | Martin | 604/43 |
| 5,429,117 | 7/1995 | McNamara et al. | 606/170 |

OTHER PUBLICATIONS

Demaria, "Management of Patients with Indeterminate Diagnostic Peritoneal Lavage Results Following Blunt Trauma," The Journal of Trauma, 31:12, 1627–31 (1991).

Lopez–Viego, "Open Versus Closed Diagnostic Peritoneal Lavage in the Evaluation of Abdominal Trauma," The American Journal of Surgery, 160 Dec. 90, 594–597.

Sherman et al, "Percutaneous Peritoneal Lavage in Blunt Trauma Patients" The Journal of Trauma, 29:6, 801–805 (1989).

Cue, "A Prospective, Randomized Comparison between Open and Closed Peritoneal Lavage Techniques," The Journal of Trauma, 30:7, 880–883 (1990).

WO 93/04726, Mar. 18, 1993, Decloux, "Catherization Placement Apparatus".

Lockhart et al, "Percutaneous Peritoneal Lavage Using the Veress Needle: A Preliminary Report," The Journal of Trauma, 27:10, 1181–84 (1987).

Feied, "Diagnostic Peritoneal Lavage," Postgraduate Medicine, 85:4, 40–49 (1989).

Ariyanayagam et al., "Diagnostic Peritoneal Lavage Using a Trocar Mounted Chest Tube," Injury, 1993 Feb. 24(2), 139.

Day et al., "Diagnostic Peritoneal Lavage: Integration with Clinical Information to Improve Diagnostic Performance," The Journal of Trauma, 32:1, 52–57 (1992).

Colucciello, "Blunt Abdominal Trauma," Emergency Medicine Clinics of North America, 11:1, 107–123 (1993).

*Primary Examiner*—Robert A. Hafer
*Assistant Examiner*—Justine Yu
*Attorney, Agent, or Firm*—Kyle W. Rost

[57] ABSTRACT

A split tipped catheter for cavitary entrance has a conical distal tip with a bore sized to receive an introducer needle. The conical tip wall is split on one side, permitting the wall to be opened by a spreading tool to clip the tip over the introducer. A fascial knife carries a blade with its tip protruding from the distal end of a backing plate, and a clip on the backing plate also engages the introducer needle for precisely incising the fascia in advance of the catheter.

29 Claims, 3 Drawing Sheets

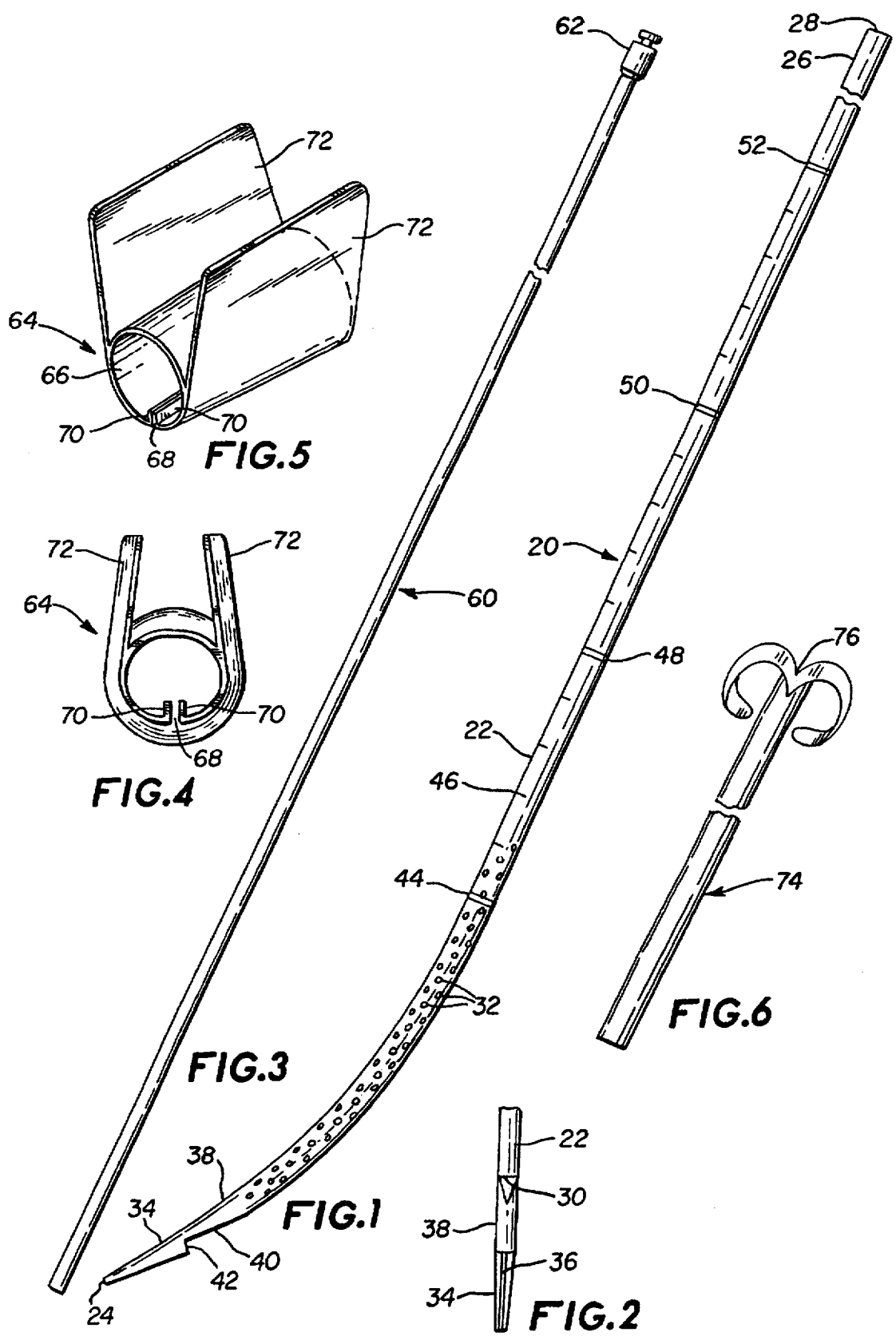

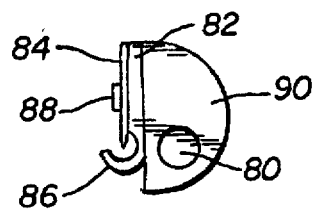
FIG.12
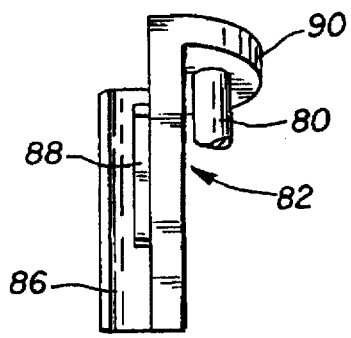
FIG.11
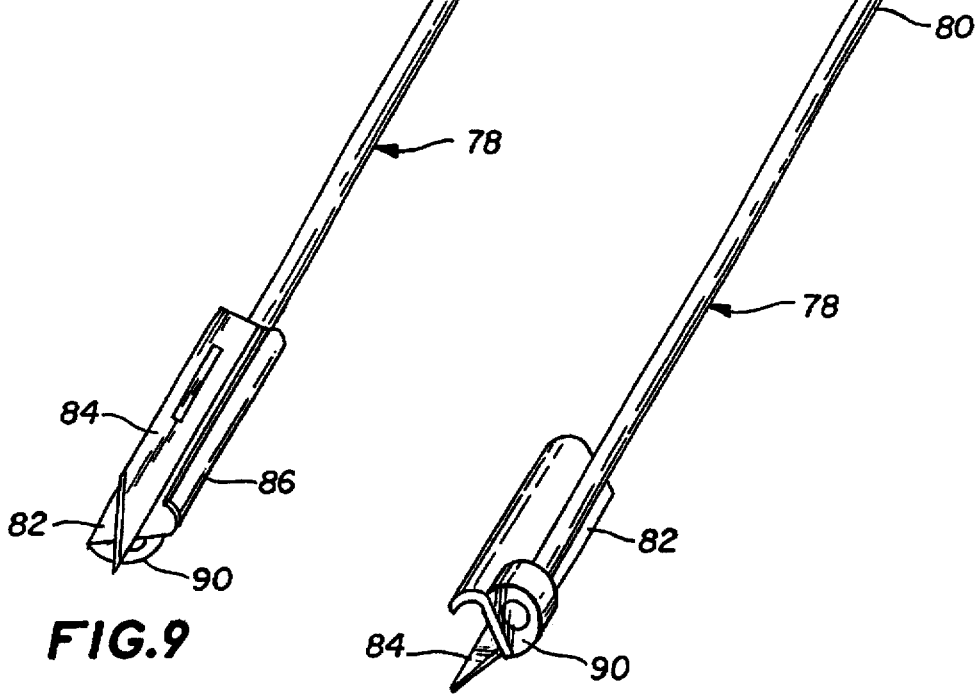
FIG.9
FIG.10

CATHETER AND METHOD OF INTRODUCTION

TECHNICAL FIELD

The invention generally relates to surgery and especially relates to a means for introducing or removing material from the body for diagnostic and therapeutic purposes, e.g., medicating, irrigating, aspirating, etc. Specifically, the treating material is introduced into or removed from a body orifice, or inserted or removed subcutaneously other than by diffusing through skin. More specifically, material is introduced or removed through a conduit, holder, or implantable reservoir inserted in the body. Still more specifically, a body entering conduit is axially movable with respect to a body piercing conduit while the former is disposed in the body. Further, the body entering conduit is provided with a longitudinal groove or slot to permit removal from the body piercing conduit. Still further, a guard is provided on the body entering conduit for preventing introduction of air during insertion of the body entering conduit. In addition, a body piercer, obturator rod, or stylet is axially moveable within the body entering conduit while the latter is disposed in the body, and a removable cover or protector is applied over the body inserted conduit. According to another aspect, the invention relates to a body inserted tubular conduit structure, e.g., needles, cannulas, nozzles, trocars, catheters, etc., and to a flexible catheter/cannula or means used therewith. The invention is a split tip catheter, together with a specially configured fascial knife and blocking sheath that significantly improves current techniques used for diagnostic peritoneal lavage.

BACKGROUND ART

Among the many applications of a catheter is diagnostic peritoneal lavage (DPL), which is the introduction of a perforated dialysis catheter into the peritoneal cavity to obtain fluid for laboratory analysis. This procedure is particularly desirable in emergency room practice in cases of abdominal trauma to determine whether intraperitoneal bleeding is present, thus distinguishing patients who need immediate laparotomy from those who do not.

Diagnostic peritoneal lavage was developed in 1965 and since then has been practiced by several techniques that have been modified and refined over time. DPL is practiced by at least three distinct techniques, which employ slightly different equipment and methods. These techniques are summarized to illustrate the equipment that has been employed. In all techniques, the patient is prepared by placement of a bladder catheter and nasogastric tube for decompression of bladder and stomach. In the first distinct technique, the closed technique, a dialysis catheter is placed through a small skin incision using a sharp trocar. This technique has been modified to reduce risk to abdominal viscera. The modified technique uses a Seldinger wire, which is termed a "wire through needle" approach. A J-tipped spring wire is passed into the pelvis through an 18-gauge short beveled introducer needle. The needle is withdrawn and a multifenestrated peritoneal lavage catheter is advanced into the pelvis over the guide wire. The J-wire is removed, and established techniques then are used to sample abdominal fluids.

Another variation of the closed technique eliminates the dialysis catheter in favor of faster acting equipment. For example, the catheter can be eliminated in favor of a chest tube mounted on a trocar. Because a chest tube has a blunt tip, it can be introduced by closed technique while still virtually eliminating the risk of intraperitoneal visceral damage.

Still another variation of the closed technique employs the Veress needle, as explained in Lockhart et al, *Percutaneous Peritoneal Lavage Using the Veress Needle: A Preliminary Report*, The Journal of Trauma, 27:10, 1181–84 (1987). The Veress needle consists of a cutting needle with a spring-loaded blunt-tipped inner cannula. In operation, the blunt obturator tip guards the cutting needle as it advances through low resistance tissue. When the needle encounters resistance, such as the fascia and peritoneum, the resistance pushes the blunt tip backwards into the needle shaft, exposing the cutting edge, which penetrates the fascia and peritoneum. When the needle again advances with less resistance, the blunt tip returns to its forward position and protect the viscera from harm. This same technique employs the 12 French introducer-dilator, which is a flexible tapered obturator covered by an outer sheath. This instrument dilates the fascia without laceration and creates a tight seal around its base. According to the procedure, a stab wound is made through the skin by a #11 blade. Then a Veress needle, sheathed with the Teflon portion of a 12-gauge angiocath, is advanced through the stab incision, fascia, and peritoneum at about 45° toward the pelvis, until advanced to the hub of the angiocath. At this point, the Veress needle is removed, leaving the angiocath in place. Then, by the Seldinger technique using a guide wire, the angiocath sheath is replaced by the 12 French obturator-introducer. The dilator and wire are removed, leaving the outer sheath in place. A standard 11F dialysis catheter is inserted through the outer sheath into the abdominal cavity, and the sheath is removed by sliding it over the straight lavage catheter. Thereafter, the lavage is performed by established techniques.

The remaining two techniques are the open and the semiopen techniques, each of which requires a longitudinal incision in the abdomen, down to the peritoneum. In open technique no trocar is required. The peritoneum is incised and opened, and under direct vision the catheter is passed downward at a 40° angle into a pelvic gutter. In semiopen technique a small incision, 2–3 mm, is incised in the fascia, but the peritoneum is unopened. Next, a trocar with an overriding catheter is popped through the peritoneum. The trocar then is removed, and abdominal fluids are sampled and tested. With the catheter in place, various established techniques allow a proper sampling of the fluid content of the abdominal cavity.

This summary of methods shows that the instruments and equipment used in diagnostic peritoneal lavage are varied, depending upon the specific technique employed. Prior techniques have employed equipment known for other purposes and adapted it for use in DPL. The present invention provides a refinement of previously known techniques and, in addition, provides an improvement in instruments and equipment that enable the new technique to be practiced. A review of patented art shows the following to be the closest known examples of possibly pertinent equipment.

In patent art there are many examples of catheter insertion needles or cannula. Those related devices were split or splittable so that they could be removed from the actual catheter after they had served their purpose of aiding insertion of the catheter. However, the known catheters and related equipment are not enabling for practice of the present invention.

For example, U.S. Pat. No. 4,773,394 to Reichstein et al, teaches a flexible intubator with a parabolic, split tip hood for covering the distal end of an endoscope during insertion. The intubator is removed by pulling it backwards over the endoscope, which opens the two leaves forming the hood. These two leaves slide up the endoscope and permit the intubator to be removed. Such an intubator is not suited for use in the present invention, due to the flexibility and parabolic shape of the tip.

U.S. Pat. No. 5,195,97 to Schiffer discloses a flexible, dual lumen balloon catheter for coronary angioplasty. This catheter has a tear strip in the wall of a guide wire lumen, which enables the surgeon to remove the catheter from the guide wire as the catheter is retracted from the body. Such a catheter is not suited for use in the present invention because of its flexibility and because once the tear strip is pulled, the catheter shape changes and its function is destroyed.

The art contains many examples of introducing cannula that are not a primary diagnostic device. Thus, such cannula would not enable the practice of DPL by the present invention. These examples include PCT Publication WO 93/04726 to Decloux, which discloses a splittable introduction cannula that enables the introduction cannula to be removed from an already inserted catheter. U.S. Pat. No. 4,883,468 to Kousai et al discloses an introduction cannula that can be removed by a split extending for its length. The split is filled with a removable strip. U.S. Pat. No. 4,412,832 to Kling et al teaches an introduction cannula that is scored so that it can be split and removed from a catheter. U.S. Pat. No. 4,776,846 to Wells discloses another splittable insertion cannula. U.S. Pat. No. Re. 31,855 to Osborne discloses a system of splittable cannula and dilators. U.S. Design Pat. 247,975 to Luther shows a split catheterization needle. The needle is split along its entire length. Opposite the split, the needle wall is perforated along another line. This device also appears to be an introducer. U.S. Pat. No. 3,550,591 to MacGregor discloses another catheterization needle that is split along its length. U.S. Pat. No. 3,713,442 to Walter is another split needle arrangement for use in "through the needle" catheter placement. U.S. Pat. No. 4,147,165 to Tauschinski shows a separable catheter insertion needle. The needle is made from two halves, which are joined together and lined with a leak-proof tube. After the catheter is inserted, the needle is split and removed.

U.S. Pat. No. 4,938,220 to Mueller, Jr. teaches a split radiopaque marker on the tip of a dilatation catheter for angioplasty to indicate location of a tip during the procedure. The "split" serves to allow a vent opening to be positioned usefully. The function is entirely different than that of the split end in the present invention.

The prior art has recognized the need to perform DPL with increased speed and cost efficiency, while avoiding damage to the viscera. Thus, it would be desirable to have suitable instruments and techniques to save time and cost, as well as to increase the safety of DPL.

Further, it would be desirable to perform DPL with increased simplicity, as enabled by an improved catheter and support equipment.

To achieve the foregoing and other objects and in accordance with the purpose of the present invention, as embodied and broadly described herein, the apparatus and method of this invention may comprise the following.

DISCLOSURE OF INVENTION

Against the described background, it is therefore a general object of the invention to provide an improved catheter and method of introduction for performing diagnostic peritoneal lavage. More specifically, the catheter and method of the invention are intended to improve safety in introducing the catheter into the abdomen. At the same time, the catheter and method can conserve critical time and reduce overall costs in patients with indications for diagnostic peritoneal lavage.

Additional objects, advantages and novel features of the invention shall be set forth in part in the description that follows, and in part will become apparent to those skilled in the art upon examination of the following or may be learned by the practice of the invention. The object and the advantages of the invention may be realized and attained by means of the instrumentalities and in combinations particularly pointed out in the appended claims.

According to one aspect of the invention, an improved catheter for insertion through tissue is of the type having a longitudinally elongated tubular body of predetermined length defined between opposite distal and proximal ends. The catheter has at least a first and a second fluid aperture defined by the elongated body at relative locations such that the first fluid aperture is relatively nearer the proximal end and the second fluid aperture is relatively nearer the distal end. The improvement is found in a bore housing of predetermined length, carded by the elongated body near the distal end, defining a bore that extends substantially longitudinally relative to the longitudinally elongated body and has a predetermined transverse dimension for, in use, carrying an introducer in sliding relationship. The bore housing is formed of juxtaposed, flexible side wall portions that define between themselves a slit extending substantially longitudinally relative to the longitudinally elongated catheter body.

According to another aspect of the invention, a catheter assembly for placing a catheter through tissue includes an elongated introducer of predetermined transverse dimension, having a distal end adapted to penetrate tissue for, in use, introducing and guiding a catheter into a body cavity. The catheter assembly also includes a catheter having a longitudinally elongated tubular body of predetermined length defined between opposite distal and proximal ends, and forming at least a fluid intake aperture and a fluid discharge aperture, wherein the fluid intake aperture is nearer the proximal end than is the fluid discharge aperture. The catheter further includes a bore housing of predetermined length, carded by the elongated body near its distal end, and defining a substantially longitudinally extending bore relative to the longitudinally elongated body. Another part of the catheter is a lateral passage means selectively moveable between open and closed positions for receiving the introducer laterally therethrough and into the bore when in open position and reclosing about the introducer in the bore when in closed position. The bore is at least as great in transverse dimension as the predetermined transverse dimension of the introducer, such that the catheter is both retained on the introducer and longitudinally slidable with respect to the introducer when the lateral passage means is in closed position about the introducer.

According to still another aspect of the invention, a method of placing a catheter through a tissue wall into a body cavity includes the steps of providing an elongated introducer of predetermined transverse dimension; and inserting a distal end of the introducer through a tissue wall and into a body cavity while maintaining the proximal end exposed outside the tissue wall. The method provides a fascial knife having an elongated handle carrying a blade support at its distal end and carrying a blade on the blade support in a position with its tip protruding beyond the distal end of the blade support. The knife also has an apparatus for selectively engaging the blade support to the introducer for slidable motion of the knife on the introducer. The fascial knife is slidably engaged with the exposed portion of the introducer. Then, the knife incises the tissue wall by advancing distally on the introducer into incising contact with the tissue wall. Thereafter, the fascial knife is disengaged from the introducer. A resilient catheter is provided, having an elongated body defining a tubular bore, carrying near a distal tip thereof an apparatus for selectively engaging the elongated body of the introducer for slidable motion of the catheter thereon; and the catheter then is slidably engaged on the exposed portion of the introducer. The distal end of the catheter is placed through the tissue wall by advancing the catheter on the introducer through the incised tissue wall; and the introducer then is withdrawn engagement with the catheter.

The accompanying drawings, which are incorporated in and form a part of the specification illustrate preferred embodiments of the present invention, and together with the description, serve to explain the principles of the invention. In the drawings:

BRIEF DESCRIPTION OF THE DRAWINGS

FIG. 1 is a side view of the split tipped catheter of the invention.

FIG. 2 is a partial bottom view of the split tip portion of the catheter.

FIG. 3 is a side view of a stiffener used with the catheter.

FIG. 4 is an partial top end view of an opening tool for the split tip.

FIG. 5 is an isometric view of the opening tool.

FIG. 6 is a side view of a sheath used with the catheter.

FIG. 9 is a front isometric view of a fascial knife.

FIG. 10 is another front isometric view of the fascial knife, rotated by 90°.

FIG. 11 is a rear isometric view of the knife backing plate.

FIG. 12 is a rear elevational view of the knife.

BEST MODE FOR CARRYING OUT THE INVENTION

Figure 7:
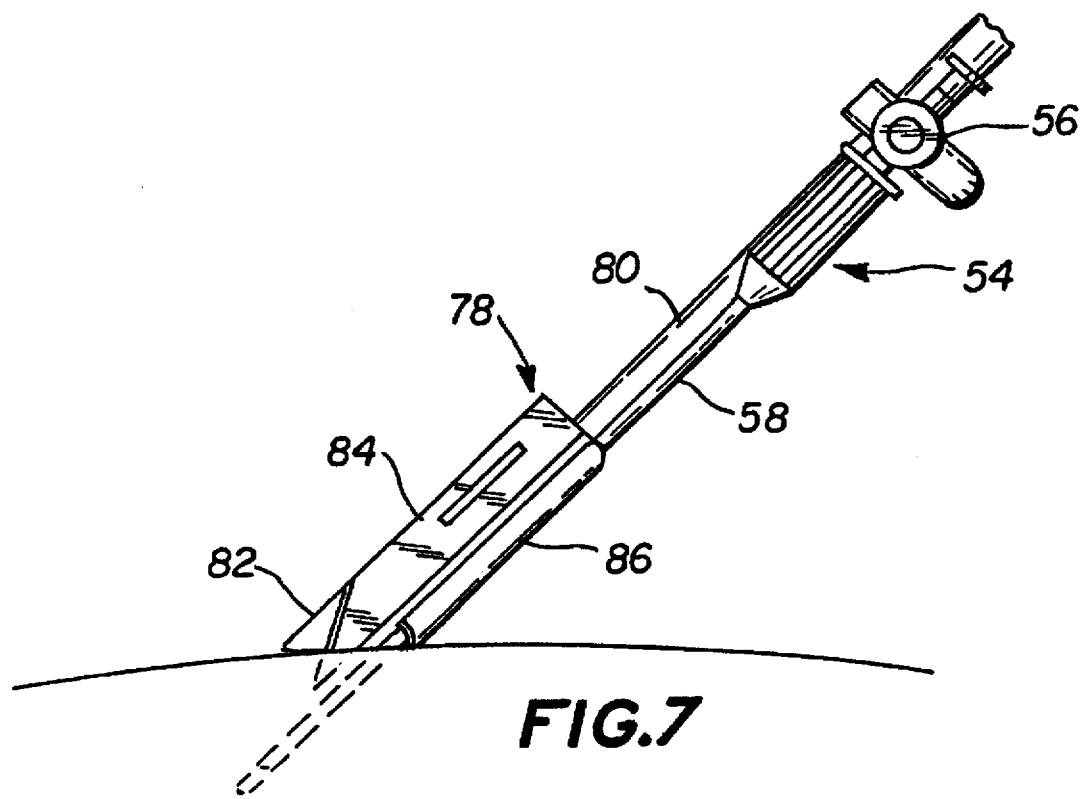
FIG. 7 is a side view of a Veress needle carrying a fascial knife, showing the knife in use to incise a tissue wall.

The invention is an improved catheter including cooperating apparatus of a catheterization system, and corresponding method of catheter introduction. One of the chief uses of the invention, although not the only use, is for performing diagnostic peritoneal lavage. This is achieved by use of a split tip catheter that can be inserted into the abdomen by clipping the tip to a Veress needle and using the needle as a guide. First, a Veress needle is introduced. Next, the catheter is clipped, via the split tip, onto the Veress needle and glided along it into the abdomen. The catheter is freed from the Veress needle when the split tip either glides off the end of the needle, or the needle is at least partially withdrawn. During insertion, a hollow trocar is placed in the catheter's main tube to straighten it and provide strength. Prior to catheter insertion, a novel fascial knife is used to incise the fascia by clipping the knife to the Veress needle, advancing it on the needle to the fascia, and incising the fascia. Other features include radiographic markings for positive identification and a blocking sheath for preventing introduction of air into the abdomen while introducing the catheter.

With reference to FIG. 1, the improved catheter 20 is of the type used for insertion through body tissue, such as a body wall, into a body cavity, such as the abdomen. In general construction, the catheter 20 has a longitudinally elongated tubular body of predetermined length. When intended for use in performing diagnostic peritoneal lavage, typically the catheter length is 33 cm. The majority of the length of this tubular body is in a shank portion 22 of predetermined, substantially uniform outside diameter. The two opposing ends of the catheter are referred to in relative terms as the distal end 24 and the proximal end 26. The length of the catheter is determined by measuring between these ends. Due to the typical tubular nature of a catheter, a central fluid bore or passageway of predetermined diameter extends longitudinally from the proximal end 26 to a point near the distal end 24. This central bore or passage is in communication with suitable fluid apertures, such as at least a first aperture 28 defined at the proximal end of the catheter, through which fluids can be passed either into or out of the catheter body. At least one other fluid aperture is found at or near the distal end. This second aperture may be an end opening, such as opening 30, FIG. 2. Alternatively or in addition thereto, the distal opening may constitute one or more perforations 32, FIG. 1, formed, for example, at a 0.32 cm. spacing, and extending through the side wall of the tubular body into communication with the central passageway. As shown in the drawing, the perforated section 34 is curved, such as on a 14 cm. radius, and extends over a length of 8.25 cm. near the distal end of the shank 22. These perforations are drainage openings and are especially suited for performing DPL. Other typical, predetermined dimensions for a DPL catheter are an outside diameter of 0.40 cm., an inside diameter of 0.34 cm., and a resultant tube wall thickness of 0.03 cm. These dimensions are merely representative examples and are not limitations. Primarily, they describe the preferred DPL catheter. In addition, the dimensions given throughout the specification can provide an approximation of the preferred relationship, fit, and proportion between parts.

At or near the distal end 24 of the catheter body is a tip or bore housing 34 that is shorter in length than the length of the catheter body. For example, this housing may have a length of 1.5 cm. as compared to a 33 cm. catheter body. This tip 34 is preferred to define the distal end of the catheter. The housing 34 forms a substantially longitudinally extending tip bore 36, which may be at least partially aligned with the tubular bore of the catheter body, such that the distal end of the tip bore opens at the furthest tip of the catheter. The length of the tip bore is approximately the same as the length of the bore housing, while the transverse dimension of the tip bore corresponds to the size required to fit over an introducer, as explained below. A typical introducer is a Veress needle having an outside diameter of 0.22 cm., in which case the inside diameter of the tip bore is 0.221 cm. These representative dimensions allow a small clearance between the bore wall and the Veress needle, such that the bore housing can be carded on the introducer needle in sliding relationship.

With reference to FIG. 2, the bore housing 34 is generally conical and longitudinally tapers toward the distal end of the catheter. When the catheter is being advanced through tissue, this taper dilates a passageway for reception of the trailing catheter body. The dilator tip may have an outer diameter of 0.36 cm., which tapers to a rounded edge at the distal end of the tip bore. The tip bore is preferred to be of substantially uniform transverse dimension, allowing the wall of the bore housing to taper in thickness. A longitudinally extending slit 36 is formed by the bore wall and extends continuously along the length of the tip bore, generally along a longitudinal axis of the catheter. Slit 36 splits one side of the tip 34 but normally is closed by the juxtaposed side wall portions of the bore housing, which are in abutting relationship. Thus, the catheter of this invention is referred to as a split tip catheter.

The bore housing of tip 34 is connected to the remainder of the catheter in such a way that both ends of the bore are exposed for passage of an introducer. At the distal end of the catheter shank 22, between the shank and the tip 34, is a tapered shank end portion 38. This portion 38 has its taper formed substantially entirely on one lateral side of the catheter, with the taper narrowing toward the distal end of the catheter. From FIG. 1 this taper can be seen to be in the general form of a notch or recess 40 in one side of the catheter, on the same side as slit 36. The recess may have a longitudinal length similar to the length of the bore housing, about 1.5 cm. The relatively larger proximal end of bore housing 34 is longitudinally juxtaposed to the relatively narrower end of portion 38, forming an end wall 42 of the recess 40. The end wall 42 is disposed at approximately a 45° angle to the longitudinal axis of the catheter, enabling a smooth removal from the body cavity when the catheter's work is done. The proximal end of the tip bore opens to the recess at this end wall 42, exposing the tip bore so that it can pass the inserter without interference from the tubular body. The depth of recess 40 may be approximately as deep as the combined predetermined transverse dimensions of the catheter shank wall and tubular passageway, so that the distal end of the tubular passageway opens into the recess without substantial obstruction.

Various markers and indicia are placed on the catheter as an aid to its operation. The entire length of the catheter may carry a radiopaque stripe or other marker, or the material of construction may have radiopaque qualities. The length of the catheter from its distal end or other useful distances may be indicated by incremental marks, such as in centimeters. Marker 44 indicates 7.25 cm. to the start of the curve, which also is the proximal end of the recess 40. Marker 46 indicates 12 cm. to the distal tip, which corresponds to the length of a Veress needle. Markers 48, 50, and 52 indicate catheter length from the distal tip as being, respectively, 15 cm., 20 cm., and 25 cm., with the progression continuing for the length of the catheter. The markings are useful for determining placement in a body cavity and determining relative position on an introducer such as a Veress needle.

The catheterization system employs the split tip catheter 20 in combination with an introducer to advance the catheter through a body wall. Many types of introducers are known in the art. A suitable introducer is an elongated rod or needle of a predetermined transverse dimension that is slightly narrower than the bore of the catheter tip 34, which allows the split tip catheter and introducer to function together properly. The introducer should have a distal end adapted to penetrate tissue, allowing the introducer to enter a body cavity and thereafter introduce and guide a catheter into the body cavity. The preferred introducer is the Veress needle 54, shown in FIGS. 7 and 8, which is a commercial product whose structure and operation are described in the prior art.

One of the improvements made possible by this catheter is the ability to clip the catheter 20 onto a Veress needle 54 or other introducer, after the introducer has been advanced into a body cavity. This is made possible by the split tip of the catheter, which is one example of a lateral passage means selectively moveable between open and closed positions for laterally receiving an introducer. The split tip of the preferred lateral passage means is formed of two juxtaposed, resilient wall portions of the bore housing 34 that define the opposite edges of slit 36 between them. These edges and the slit itself extend substantially longitudinally relative to the catheter body so that the catheter is placed on the introducer in position to be advanced along the introducer. The prior art generally has lacked the practical ability to mount a catheter onto the exterior surface of an introducer that already has been placed, especially when the introducer has a substantial head structure 56 as found on the Veress needle. However, the catheter 20 of this invention has the ability to receive the needle shaft 58 laterally into the tip bore. More importantly, the bore housing 34 is capable of being selectively configured into either an open position or a closed position. When in open position, the walls at the edges of the slit have been spread from their usual closed position, opening the slit 36 by at least a sufficient width to receive the introducer needle laterally through the slit and into the tip bore. When in closed position, the sides of the slit are abutting and in mutual contact, or as close thereto as possible. A full closure of the slit is desirable to prevent tissue damage as the catheter is advanced through tissue.

After the bore housing has been opened and the introducer needle has been placed through the slit into the tip bore, the slit is closed around the introducer needle. In order for the bore housing to fully reclose the slit when returned to closed position, the tip bore must be at least as great in transverse dimension as the predetermined transverse dimension of the introducer. Thus, the preferred bore diameter is 0.001 cm. greater than the diameter of the Veress needle. The greater size of the bore permits the catheter to be both retained on the introducer and longitudinally slidable with respect to the introducer when the lateral passage means is in closed position about the introducer.

The catheter is preferred to be constructed from a plastic, elastomer, or other synthetic material having resilience and shape memory. Polyethylene is a preferred material. The catheter tip is considered semi-rigid and nondeformable in its typical use. When the tip clips over a guiding needle, it firmly retains its engagement on the needle. Further, the tip retains its shape during advancement through tissue and insertion into a body cavity. One reason why this tip must be substantially nondeformable in use is that the tip is required to dilate the fascia as it enters the body cavity. Due to these requirements, an assisting tool is used for the task of opening the split tip and may assist in returning it to closed position. After the tip is opened, the resilience and memory of the synthetic material also are useful to reclose the tip. Further, the illustrated catheter 20 of FIG. 1 has a curved portion of the shank 22. However, during insertion along an introducer needle, the catheter should be straight. Another assisting tool is used for the task of straightening the catheter, as well as adding rigidity during the insertion process. These are described below.

FIG. 3 illustrates a stiffening means that is received in the tubular passageway of the catheter 20 for stiffening the catheter and for advancing the catheter along the introducer after the catheter has been retained on the introducer. The stiffening means is a trocar or obturator 60. For use with the preferred catheter as described above, the obturator has an outer diameter of 0.24 cm. and a length of 30 cm. The proximal end of the obturator carries a head such as a Leur-lock tip 62, which serves both as a stop to limit entry into the catheter passageway and as a grip for removal. In addition, a Leur-lock tip 62 provides a conventional junction for introducing fluids such as saline through a trocar. The length of the obturator is sufficient to penetrate the catheter through the curved portion, temporarily straightening the curve. The distal end of the obturator reaches as far as the end of the curve, terminating at the proximal end of the recess 40. The typical clearance between the obturator and the catheter passageway is 0.002 cm., measured radially, which permits the obturator to be inserted or removed freely and provides room for added saline to block air passage. The trocar or obturator is inserted into the catheter body before the catheter is clipped onto the introducer.

In order to clip the catheter onto the introducer, an opening means is used to move the tip into open position. FIGS. 4 and 5 show one suitable opening tool 64. The tool is constructed of a conical shell 66 configured to fit closely over conical catheter tip 34. Shell 66 defines a generally axially extending division 68 along one side of the shell. Along each side of the division 68 is one of two inwardly extending lips 70. A pair of shell opening levers 72 are connected to the conical shell 66 on opposite sides of the division 68. These levers spread apart the two lips 70 by relative movement of the levers 72, such as by pinching together the levers. The opening tool is constructed as a unitary member of a strong, resilient material such as spring steel. In use, the shell 66 is positionable over the conical tip of the catheter to locate the division 68 over the slit 36 in the catheter tip. More specifically, the shell is slid axially onto the conical tip so that the lips 70 enter the slit 36 and engage the opposite sides of the slit when the division 68 is positioned over the slit. When the levers 74 are pinched together, the lips are spread, thereby opening the slit. When the catheter tip has been moved over the introducer needle and the needle is seated in the tip bore, the levers are released. The resiliency of the spring steel closes the shell, squeezing the conical tip toward closed position. The shell is removed by sliding it axially from the tip, removing the lips 70 from the slit 36.

Still another component of the catheterization system is a sleeve or blocking sheath 74, shown in FIG. 6. This sheath slides over the shank of the catheter and allows the catheter to be introduced without introducing air into the abdomen or other cavity. In incomplete entry of the catheter, the sheath can be positioned to block lavage holes 32 and allow initial aspiration. Typically, a sheath has a length of 15 cm., an inner diameter of 0.401 cm., and an outer diameter of 0.461 cm. The side walls may be scored with parting lines 76 that enable the sheath to be removed by splitting after its function is complete.

The catheterization system anticipates that the catheter 20 can be placed with minimal intrusion to the body. Accordingly, during placement the related incision is minimized by use of a fascial knife 78 that precisely incises the required opening by employing the introducer needle as a guide. FIGS. 9-12 illustrate the structure of the preferred knife 78. An elongated, flexible handle 80 carries a blade support 82 at its distal end. The blade support carries a conventional surgical blade 84, such as a Bard-Parker No. 11, in a position with the blade tip projecting by ⅛ inch from the distal end of the blade support. The preferred blade, the Bard-Parker No. 11, has its sharp edge extending from a distal point, angling acutely rearwardly along one side only, as shown in FIGS. 9 and 10. The blade support carries a means for selectively engaging the blade support to the introducer, which permits the fascial knife to be engaged with the introducer for slidable motion. The preferred engaging means is a clip 86 located along a longitudinal side edge of the blade support. This clip is C-shaped in transverse cross-section, provides an elongated channel that extends substantially parallel to the elongated knife handle, and is sized to receive the introducer. As shown in FIG. 7, when the clip 86 is engaged on the introducer, the clip maintains handle 80 in a position substantially parallel to the introducer. In this position, the knife can be advanced along the introducer until the blade incises the fascia. The backing plate positions the blade in juxtaposed position to the introducer, with its non-sharp edge against the introducer or nearly so. In this position relative to the introducer, the blade point initiaties the incision at the side of the introducer and incises a small opening that is substantially continuous with the puncture formed by the introducer. After the fascia is incised, the knife is withdrawn and disengaged from the introducer.

With reference to FIGS. 11 and 12, the blade support 82 provides a planar backing plate that carries a blade mounting boss 88 on its face. The position of the boss 88 determines the relative position of the blade against the backing plate and establishes the ⅛ inch projection of the blade point. The distal end of the backing plate is disposed at an acute angle of about 40° to the axis of the knife handle, which is the preferred angle of the introducer and knife during the incision process. In addition, the blade support carries a means for limiting penetration of the blade during incising contact with the tissue wall. To a small extent, the distal end of the blade support itself serves as a stop. However, the preferred penetration limiting means is a planar platform 90 molded to the face of the blade support opposite from the mounting boss 88 and at the distal end, extending normally to the plane of the backing plate, and disposed at the acute angle of the distal edge of the backing plate. The knife handle 80 is preferred to be molded to the proximal face of the platform 90, in the position shown in FIG. 12, which provides a small offset of the handle from the introducer needle when the knife is mounted thereon. The knife handle may carry marking indicia similar to those on the catheter, as an aid to use. For example, the knife handle may carry markers at centimeter intervals, measured from the blade tip, to provide an indication of the position of the blade.

Because the catheterization system has many uses, only a limited and general description of its use can be broadly applicable. In order to place the catheter 20 through a tissue wall into a body cavity, the first step is to provide an elongated introducer of predetermined transverse dimension. As noted, a Veress needle 54 is the preferred introducer. Next, the distal end of the introducer is inserted through a tissue wall and into a body cavity, while the proximal end of the introducer is maintained outside the tissue wall to receive the fascial knife and catheter. Then, a fascial knife is supplied, of the type described above, having an elongated handle carrying a blade support at its distal end, with a blade positioned on the blade support with its tip protruding by a desired amount. The knife includes an engaging means such as the clip 86, which allows the knife to slide along the introducer. The knife is attached to the exposed portion of the introducer by the engaging means or clip 86, and advanced distally on the introducer until it incises the tissue wall. The knife then is withdrawn and disengaged from the introducer.

After the small incision has been made, the catheter can be placed. The process requires that a suitable catheter be provided, having an elongated body defining a tubular bore, and having a means such as a split tip for engaging the catheter body on the introducer. If the catheter has a plurality of drainage perforations through its side wall, a catheter sheath may be placed over the catheter, in sealing relationship over the drainage perforations. In most instances the rigidity of the catheter will be increased by inserting a hollow trocar into the tubular bore of the catheter. Then, the catheter is suitably engaged with the exposed portion of the introducer and advanced along the introducer by sliding motion. The catheter tip is advanced through the incised tissue wall, while the tip dilates an opening to receive the trailing catheter body. When the catheter tip has been advanced through the tissue wall, the introducer is withdrawn. Thereafter, the catheter can be further advanced into the cavity, as required.

The preferred embodiment of the catheter as illustrated in the drawings is specifically adapted for use in performing diagnostic peritoneal lavage. The steps for this procedure, using the catheter and method of this invention, are as follows:

First, according to conventional practice for performing DPL, insert a urethral catheter and levine tube. Surgically prepare and drape the abdomen. Locally anesthetize the upper rim of the umbilicus and an area 1 cm cephalad to the umbilicus and 1 cm lateral to the midline with 1% lidocaine and epinephrine.

Next, with specific reference to the method of the invention, if it is intended not to introduce air into the abdomen, place the sheath 74 over the proximal end of the catheter 20. Straighten the catheter curve by inserting the hollow trocar 60 into the catheter 20. Make a 1 cm transverse incision in the anesthetized area. Elevate the umbilicus at the anesthetized area with a towel clip. The Veress needle includes a saline reservoir and red ball indicator that signal when the needle has completed its penetration of a tissue wall. Insert the Veress needle 54 through the incision at 90° to the surface, with the saline reservoir then being filled and the red ball indicator floating. When the red ball indicator falls, stop insertion as the needle is in the abdominal peritoneal cavity.

Aim the Veress needle caudally to 40°, attach the fascial knife 78 to the Veress needle and incise the fascia caudad from the needle, as illustrated in FIG. 7. A #11 Bard-Parker blade should be attached to the fascial knife for performing this step.

Figure 8:
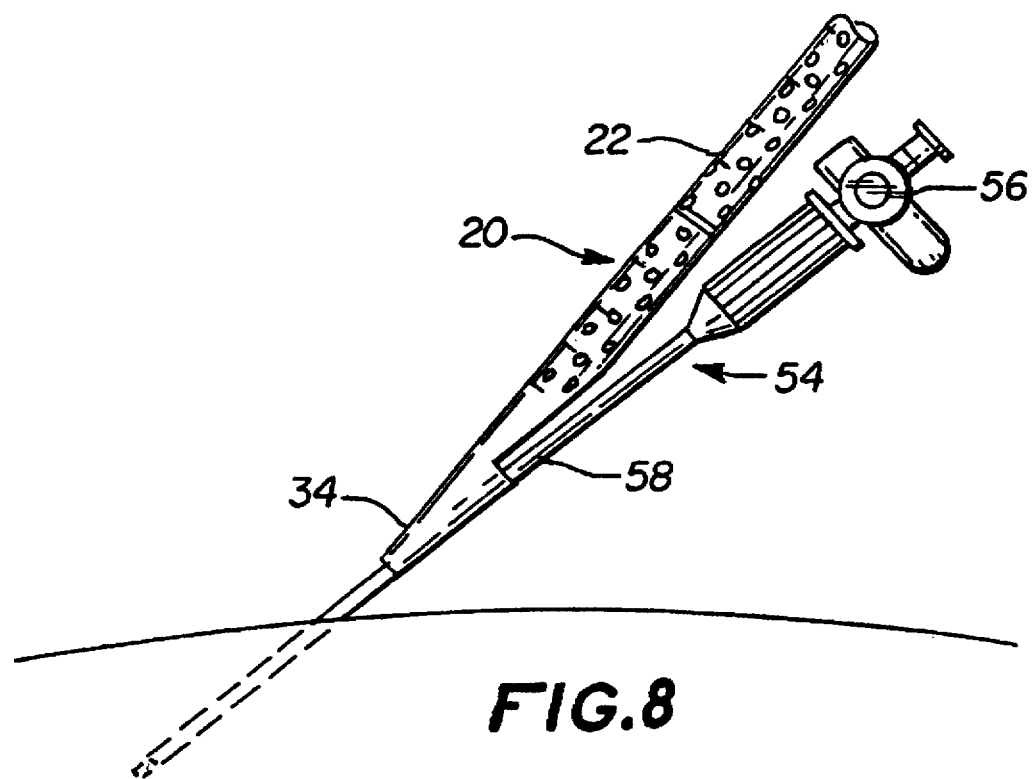
FIG. 8 is a side view of a Veress needle carrying the catheter, showing the catheter in position to be introduced through a tissue wall.

Clip the catheter 20 to the caudad surface of the Veress needle as shown in FIG. 8 and slide the catheter along the needle into the abdomen. Alternatively, if air is not to be introduced, insert catheter 20 just past the fascia and fill the catheter with saline through the hollow trocar tube 60 as the tube is withdrawn. Prior to filling the catheter with saline, slide the sheath 74 down over the drainage perforations 32.

Remove the Veress needle while advancing the catheter into a pararectal gutter.

Thereafter, the DPL is completed according to the following known procedures. Aspirate the catheter for gross blood. Insert 20 cc/Kg, 1000 cc maximum of warmed ringers lactate and remove at least 200 cc for each DPL. If time permits, agitate the abdomen gently and wait 5 to 10 minutes. Lower the lactated fingers bag, which is a closed system and must not have an air lock, to the floor for siphonage.

The foregoing is considered as illustrative only of the principles of the invention. Further, since numerous modifications and changes will readily occur to those skilled in the art, it is not desired to limit the invention to the exact construction and operation shown and described, and accordingly all suitable modifications and equivalents may be regarded as falling within the scope of the invention as defined by the claims that follow.

We claim:

1. An improved catheter for insertion through tissue, of the type having a longitudinally elongated tubular body of predetermined length defined between opposite distal and proximal ends, said tubular body defining at least a first and a second fluid aperture at relative locations such that the first fluid aperture is relatively nearer said proximal end of the tubular body and the second fluid aperture is relatively nearer said distal end of the tubular body, wherein the improvement comprises:

a bore housing of predetermined length, carried by said elongated body near the distal end thereof, defining a bore extending substantially longitudinally relative to the longitudinally elongated body and of predetermined transverse dimension for, in use, carrying an introducer in sliding relationship therein;

wherein:
said bore housing comprises juxtaposed side wall portions defining a slit therebetween extending the entire length of said bore;
said side wall portions are sufficiently rigid to retain shape during advancement through body tissue; and
the catheter is configured in a curve and has shape memory allowing manipulation within a body cavity after insertion therein.

2. The catheter of claim 1, wherein the predetermined length of said bore housing is shorter than the predetermined length of said elongated body.

3. The catheter of claim 1, wherein said bore housing is longitudinally tapered, having a relatively narrower distal end than proximal end, for, in use during insertion through tissue, dilating an opening.

4. The catheter of claim 1, wherein the bore defined by said bore housing is substantially uniform in transverse dimension.

5. The catheter of claim 1, wherein said slit extends longitudinally of the bore housing.

6. The catheter of claim 1, wherein said bore housing is located at the distal end of said elongated catheter body.

7. The catheter of claim 6, wherein the bore defined by said bore housing has its distal end located at the distal end of said elongated catheter body.

8. The catheter of claim 1, wherein said first fluid aperture defined by said elongated body is located at said proximal end thereof; and said second fluid aperture defined by the elongated body comprises a perforation formed in a side wall thereof.

9. The catheter of claim 8, further comprising a plurality of second fluid apertures.

10. The catheter of claim 1, wherein:
said elongated body comprises a shank portion of substantially uniform transverse dimension and further comprises a shank distal end portion having a taper formed substantially on one lateral side of said shank distal end portion and tapering toward the distal end of the elongated body;
said bore housing is longitudinally juxtaposed to the shank end portion of the body, forming the distal tip of the catheter, and the proximal end of the bore housing is of larger transverse dimension than the distal end of the shank end portion; and
the shank distal end portion defines a recess at its junction with the bore housing, and the proximal end of the bore opens to said recess for, in use, receiving an elongated inserter through the bore.

11. The catheter of claim 10, wherein:
said tubular body is comprised of a body wall of predetermined transverse dimension, defining an elongated central passageway in communication with said first and second apertures, and wherein the central passageway is of a predetermined transverse dimension; and
the recess defined by said shank end portion is at least as deep as the combined predetermined transverse dimensions of said body wall and central passageway, such that the distal end of said central passageway opens into said recess without substantial obstruction.

12. A catheter assembly for cavitary entrance through tissue, comprising;
    an elongated introducer of predetermined transverse dimension, having a relatively narrower distal and suited, in use, for penetrating tissue while introducing and guiding a catheter into a body cavity;
    a catheter having a longitudinally elongated tubular body of predetermined length defined between opposite distal and proximal ends, and forming at least a first and a second fluid aperture wherein the first fluid aperture is relatively nearer said proximal end than is the second fluid aperture;
    a bore housing of predetermined length, carried by said elongated body near the distal end thereof, defining a substantially longitudinally extending bore relative to the longitudinally elongated body; and
    a lateral passage means selectively moveable between open and closed positions for receiving said introducer laterally therethrough and into said bore when in open position and laterally retaining the introducer in the bore when in closed position, wherein said lateral passage means is sufficiently rigid to retain shape during advancement through body tissue;
    wherein said bore is at least as great a transverse dimension as the predetermined transverse dimension of the introducer, such that the catheter is both retained on the introducer and longitudinally slidable with respect to the introducer when the lateral passage means is in closed position about the introducer; and
    wherein the lateral passage means comprises two resilient wall portions of said bore housing defining a slit therebetween continuously extending over the length of said bore.

13. The catheter assembly of claim 12, wherein said catheter defines a tubular passage longitudinally therethrough, and further comprises:
    a stiffening means received in said tubular passage for stiffening the catheter and for advancing the catheter along the introducer when the catheter is retained on the introducer.

14. The catheter assembly of claim 13, wherein said stiffening means comprises a trocar.

15. The catheter assembly of claim 13, wherein said catheter is constructed of a resilient material; and
    wherein said stiffening means comprises a substantially straight trocar received in said tubular passage and straightening the catheter.

16. A method of placing a catheter through a tissue wall into a body cavity, comprising:
    providing an elongated introducer of predetermined transverse dimension;
    inserting a distal end of said introducer through a tissue wall and into a body cavity while maintaining the proximal end exposed outside the tissue wall;
    providing a fascial knife comprising:
        an elongated handle carrying a blade support at its distal end and carrying a blade on said blade support positioned with its tip protruding beyond the distal end of the blade support; and
        a means for selectively engaging the blade support with the introducer for slidable relative motion;
    engaging the fascial/knife with the exposed portion of the introducer for slidable motion thereon;
    incising the tissue wall by advancing the fascial knife distally on the introducer into incising contact with the tissue wall;
    disengaging the fascial knife from the introducer;
    providing a resilient catheter having a longitudinally elongated tubular body of predetermined length defined between opposite distal and proximal ends, said tubular body defined at least a first and a second fluid aperture at relative location such that the first fluid aperture is relatively nearer said proximal end of the tubular body and the second fluid aperture is relatively nearer said distal end of the tubular body; the tubular body further defining a means for selectively engaging the elongated body with the introducer for slidable motion of the catheter thereon, comprising a bore housing of predetermined length, carried by said elongated body near the distal end thereof, defining a bore extending substantial, longitudinally relative to the longitudinally elongated body and of predetermined transverse dimension for carrying an introducer in sliding relationship therein, said bore housing comprising juxtaposed side wall portions defining a slit therebetween extending the entire length of said bore; wherein said side wall portions are sufficiently rigid to retain shape during advancement through body tissue; and wherein the catheter is configured in a curve and has shape memory allowing manipulation within a body cavity after insertion therein;
    engaging the catheter on the exposed portion of the introducer for slidable motion thereon;
    placing the distal end of the catheter through the tissue wall by advancing the catheter on the introducer through the incised tissue wall; and
    withdrawing the introducer from engagement with the catheter.

17. The method of claim 16, wherein:
    said blade is of the type having a pointed tip with a sharp edge extending acutely rearwardly therefrom; and
    said blade support carries the blade in a position, relative to said means for engaging the blade support with the introducer, that said blade tip is juxtaposed to the introducer and said sharp edge faces away from the introducer.

18. The method of claim 16, wherein said introducer comprises a Veress needle.

19. The method of claim 16, wherein said blade support further comprises a means for limiting penetration of the blade during incising contact with the tissue wall.

20. The method of claim 19, wherein said means for limiting penetration comprises a stop.

21. The method of claim 20, wherein said stop is disposed at an acute angle with respect to said elongated handle.

22. The method of claim 16, wherein said means for engaging the blade support to the introducer comprises a clip carded by the blade support.

23. The method of claim 22, wherein said clip defines a channel receiving the introducer and extending substantially parallel to the elongated handle, such that the clip maintains the handle substantially parallel to the introducer when the clip is engaged on the introducer.

24. The method of claim 16, wherein said bore housing further comprises a conical tip having the slit defined in a side wall thereof, wherein said side wall is moveable between open and closed positions of the slit, the open position of the slit being at least as wide as said predetermined transverse dimension of the introducer, permitting reception of the introducer laterally through the slit and into the tip bore.

25. The method of claim 24, further comprising, prior to said step of engaging the catheter to the introducer, providing a slit opening means for moving said tip wall into open position of the slit.

26. The method of claim 25, wherein said slit opening means comprises:

- a conical shell configured to fit closely over said conical tip;
- said shell defining a generally axially extending division along one side of the shell, said shell being positionable over the conical tip to locate the division over the slit of the tip;
- two inwardly extending lips, one such lip being disposed on the shell along each side of the division, said lips being positioned to enter the slit and engage the opposite sides of the slit when the division is positioned over the slit; and
- a pair of shell opening levers connected to the conical shell on opposite sides of the division, spreading apart the two lips by relative movement of the levers, opening the slit by separating the opposite sides of the slit when the lips engage the opposite sides of the slit.

27. The method of claim 26, wherein said conical tip is formed of a resilient material, such that the opposite sides of the slit are retainable to closed position of the slit after being moved to open position.

28. The method of claim 16, further comprising, prior to engaging the catheter on the introducer, increasing the rigidity of the catheter by inserting a hollow trocar into the tubular bore of the catheter.

29. The method of claim 16, wherein said catheter defines a plurality of drainage perforations through the side wall thereof near its distal end, and said step of providing a catheter further comprises: providing a catheter sheath over the catheter, wherein said sheath is slidable in sealing relationship over said drainage perforations.

* * * * *